US009980848B2

(12) United States Patent
Gilmer et al.

(10) Patent No.: US 9,980,848 B2
(45) Date of Patent: May 29, 2018

(54) FORCE DISTRIBUTION METHOD AND APPARATUS FOR NEONATES AT RISK OF CRANIAL MOLDING

(71) Applicant: Invictus Medical, Inc., San Antonio, TX (US)

(72) Inventors: Christopher Loring Gilmer, Carmel, IN (US); Thomas Craig Roberts, San Antonio, TX (US); Samuel Alexander, Des Moines, IA (US); George Martin Hutchinson, San Antonio, TX (US); Daniel V. Mendez, San Antonio, TX (US)

(*) Notice: Subject to any disclaimer, the term of this patent is extended or adjusted under 35 U.S.C. 154(b) by 371 days.

(21) Appl. No.: 14/854,774

(22) Filed: Sep. 15, 2015

(65) Prior Publication Data

US 2016/0038332 A1    Feb. 11, 2016

Related U.S. Application Data

(63) Continuation of application No. 14/504,404, filed on Oct. 1, 2014, now Pat. No. 9,173,763.

(60) Provisional application No. 62/012,795, filed on Jun. 16, 2014, provisional application No. 61/947,203, filed on Mar. 3, 2014, provisional application No. 61/885,486, filed on Oct. 1, 2013.

(51) Int. Cl.
*A61F 5/055*    (2006.01)
*A61F 5/058*    (2006.01)
*A61F 5/01*    (2006.01)

(52) U.S. Cl.
CPC ........ *A61F 5/05891* (2013.01); *A61F 5/0102* (2013.01); *A61F 5/05883* (2013.01)

(58) Field of Classification Search
CPC .. A61F 5/055; A61F 13/12; A61F 5/34; A61F 11/14; A61F 11/06; A61F 5/05891; A61F 5/0102; A45D 44/22; A61B 6/0421; A61B 5/0555; A42B 3/166
See application file for complete search history.

(56) References Cited

U.S. PATENT DOCUMENTS 3,171,133 A    3/1965  Steffen
4,581,773 A    4/1986  Cunnane
(Continued)

FOREIGN PATENT DOCUMENTS

WO  PCT/US2014/058709    10/2014

OTHER PUBLICATIONS

U.S. Appl. No. 29/511,677, filed Dec. 12, 2014, Gilmer et al.
(Continued)

*Primary Examiner* — Ophelia A Hawthorne
(74) *Attorney, Agent, or Firm* — Robert A. Lawler

(57) ABSTRACT

A force distribution apparatus and method are presented. Various embodiments of the disclosed apparatus include a plurality of layers configured and oriented to be deployed on a subject in a manner that disperses forces and lowers peak pressures experienced by the subject when resting on a surface, which tends to minimize risks of deformation and local ischemia. An innovative combination of novel construction methods and material selections produce an apparatus that possesses an inherent three-dimensional shape despite being built from essentially flat components, while also retaining an ability to effectively distribute forces and reduce pressures.

29 Claims, 4 Drawing Sheets

(56) References Cited

U.S. PATENT DOCUMENTS

| | | | |
|---|---|---|---|
| 4,663,785 | A | 5/1987 | Comparetto |
| 5,243,709 | A | 9/1993 | Sheehan et al. |
| 5,815,846 | A | 10/1998 | Calonge |
| 5,978,972 | A | 11/1999 | Stewart et al. |
| 6,427,253 | B1 | 8/2002 | Penny |
| 6,428,494 | B1 | 8/2002 | Schwenn et al. |
| 6,493,881 | B1 | 12/2002 | Picotte |
| 6,625,820 | B1 | 9/2003 | Lampe |
| 6,939,316 | B2 | 9/2005 | Sklar et al. |
| 7,036,156 | B2 | 5/2006 | Lahman et al. |
| 7,563,237 | B1 | 7/2009 | Murphy |
| 7,761,933 | B2 | 7/2010 | Pham |
| 2002/0166157 | A1 | 11/2002 | Pope |
| 2004/0107482 | A1 | 6/2004 | Picotte |
| 2007/0000025 | A1 | 1/2007 | Picotte |
| 2007/0199151 | A1 | 8/2007 | Brown et al. |
| 2013/0046219 | A1* | 2/2013 | Mendez ................ A61F 13/12 602/17 |

OTHER PUBLICATIONS

International Search Report and Written Opinion for International Application No. PCT/US2014/058709, dated Jan. 14, 2015, 8 pages.

\* cited by examiner

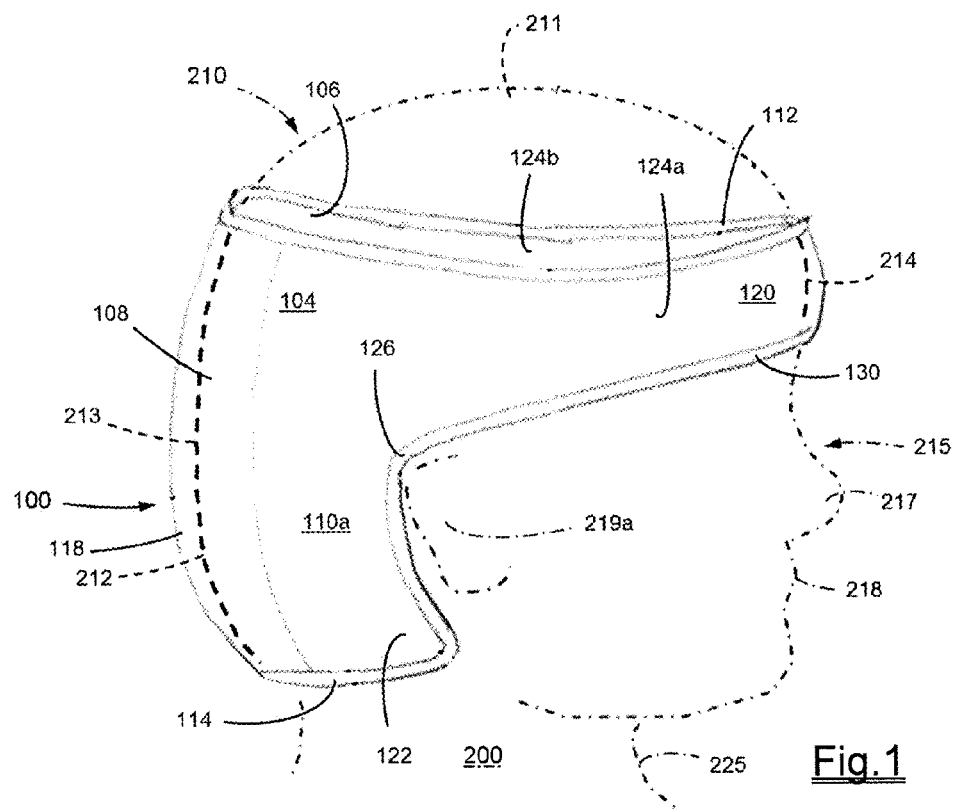
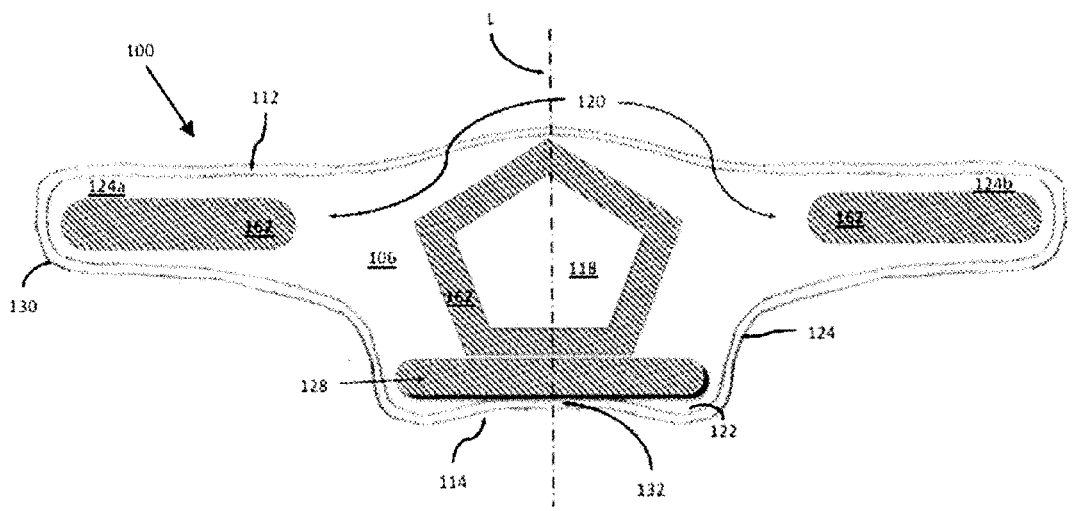

FORCE DISTRIBUTION METHOD AND APPARATUS FOR NEONATES AT RISK OF CRANIAL MOLDING

CROSS-REFERENCE TO RELATED APPLICATIONS

This application is a continuation of and claims priority benefit of U.S. application Ser. No. 14/504,404, filed Oct. 1, 2015, now U.S. Pat. No. 9,173,763, which claims priority to U.S. Provisional Application Ser. No. 62/012,795, filed Jun. 16, 2014, entitled "Pressure Distribution for Neonates at Risk of Cranial Molding", to U.S. Provisional Application 61/885,486, filed Oct. 1, 2013, entitled "Bonnet For Preventing & Treating Neonatal Cranial Molding & Skin Breakdown", and to U.S. Provisional Application Ser. No. 61/947,203 filed Mar. 3, 2014, entitled "Pressure Distribution for Neonates at Risk of Cranial Molding", the contents of each of which are incorporated herein in their entireties by this reference. This application also references U.S. Non-Provisional application Ser. No. 13/642,034, filed Apr. 21, 2011, entitled "Neonatal Cranial Support Bonnet", which claims priority to provisional application U.S. Provisional Application Ser. No. 61/327,647, filed Apr. 23, 2010, both of which are also incorporated herein in their entirety by this reference.

BACKGROUND OF INVENTION

1. Field of the Invention

The present invention particularly relates to medical devices and methods that prevent, minimize and/or treat cranial molding in neonatal subjects, most especially for human subjects born prematurely. More particularly, the present invention relates to such medical devices and methods that distribute cranial interface pressures and corresponding forces routinely encountered during care of such neonatal subjects, primarily for reducing risks of cranial deformation and potentially associated developmental impairment or delay.

2. Description of Related Art

As a neonatal human subject lies in a supine position, forces are imparted at areas of contact between the subject and the surface on which the subject lies. When the subject is lying in a supine (back downward) position, a contact area exists generally on the occipital region of the subject's head.

In the mid-1990s, the "Back to Sleep" (BTS) campaign was initiated to address the problem of sudden infant death syndrome (SIDS). It was hypothesized that a risk factor associated with SIDS in infants was sleeping in a prone position and that switching infants to a supine position that the incidence of SIDS would decrease. In one study of 568 SIDS cases occurring before and after the initiation of the BTS campaign in about 1994, a sudden decrease in the rate of SIDS cases from 1.34 per 1,000 births in 1991 to 0.64 per 1,000 births in 2008 occurred. The study also showed that, over that same period, the percentage of SIDS infants placed to sleep prone decreased from 85.4% to 30.1% and that those found prone decreased from 84.0% to 48.5%, whereas those placed supine increased from 1.9% to 47.1%. Such findings indicate overall that more infants were placed supine at the time that the SIDS rate was declining precipitously (Trachtenburg F L et al, "Risk Factor Changes for Sudden Infant Death Syndrome After Initiation of Back-to-Sleep Campaign", Pediatrics 2012; 129; 630).

Largely attributed to the BTS campaign, there has been a simultaneous increase in the occurrence of cranial molding, including deformational plagiocephaly. Deformational plagiocephaly (DP) refers to asymmetry or flattening of the infant skull secondary to external force. While DP has long been an occasional condition in neonatal subjects in general, the incidence of DP has steadily increased over the past twenty years, from an estimated 5% in the mid-1990s to 20-30% currently. Such cranial deformation, unfortunately, may not merely be a cosmetic condition. Evidence suggests that children with deformational plagiocephaly have an increased risk for developmental impairment or developmental delay, perhaps because brain parenchyma shifts to conform to positional skull deformities.

In spite of the long history and steady increase in the incidence of cranial molding, optimal solutions have not been presented. It is known that some orthotics are used in an attempt to ameliorate such conditions, yet the cranial molding rate remains high, and many other challenges and obstacles encountered with the prior art remain unresolved.

Many other advantages, disadvantages, problems and challenges of the prior art are known and will be evident to those of ordinary skill in the art, particularly after reading this specification and contemplating its implications.

BRIEF SUMMARY OF THE INVENTION

It is a fundamental object of the present invention to minimize and overcome the obstacles and challenges of the prior art, especially in ways that contribute to improved health and wellbeing of those who are suffering or are at risk of suffering from deformational plagiocephaly, as well as to facilitate and enable effective yet easy and affordable interventions and techniques for achieving such improved health and wellbeing. While numerous secondary objects may also be addressed, the most pressing objectives relate especially to the care of neonatal human subjects who are born prematurely and who suffer or are at risk of suffering complications due to cranial molding and related developmental conditions.

In the following descriptions and accompanying drawings, numerous details are set forth and illustrated to provide a more thorough understanding of preferred embodiments of the present invention. It will be apparent, however, to one skilled in the art, that embodiments of the present invention may be practiced without these specific details. As used herein, unless otherwise indicated, "or" does not require mutual exclusivity.

In many embodiments of the invention, force-distributing apparatus are provided for use on a subject such as a human. Such force-distributing apparatus are generally adapted to disperse the forces imparted to the subject's tissue due to the weight of the subject on an external support surface, thereby reducing the pressure resulting from the applied force. Preferred embodiments of the present invention are often in the form of a force-distributing cranial support, which is sometimes referred to as a pressure reducing cranial support, a force-distributing apparatus, a "bonnet", or a "protector." In some embodiments, the force-distributing cranial support is designed, structured, sized, and secured to a subject's head in order to distribute cranial and skin interface pressures while reducing point loads encountered between the subject's head and a mattress, pad or other underlying support surface on which the subject's head is positioned to rest. In other embodiments, the pressure reducing cranial support is designed, structured, and sized to be positioned on a pediatric head and in other embodiments on an adult head. The pressure reduction apparatus may take other forms permitting the pressure reduction apparatus to be affixed over a bony protuberance of the human, the bony protuberance including but not limited to a pelvic region, an elbow, or the heel of the foot.

When so placed on the subject, the force-distributing apparatus, because of its particular features and characteristics, distributes external forces away from the area of contact between the tissue and an external surface, as smaller forces over a larger area. Such smaller forces over the larger area, in turn, result in less applied pressure. Accordingly, without being limited to any particular theory, by distributing the normal forces applied to the cranial bones when the infant is laying supine, the infant's brain parenchyma within the cranial cavity may be more likely to grow essentially in a radial manner and less likely to have growth restricted to cranial portions not experiencing high normal forces.

When affixed to the head of the infant, the force-distributing cranial support is configured to reduce compressive forces on soft, flexible cranial plates that define a cranial cavity. The force-distributing cranial support cradles the head, further promoting the proper development of the infant's head, reducing the incidence or preventing the development of plagiocephaly, brachycephaly, and dolichocephaly (referred to collectively as, "positional cranial molding" or, simply, "cranial molding"), as well as other forms of skeletal deformation. Such reduction of the development of cranial molding is also thought to aid in the prevention and treatment of other related disorders and diseases in neonatal subjects—most notably by permitting the normal growth of brain tissue within the cranial cavity, perhaps positively affecting cognitive development.

Though not the primary object of the present invention, due to the surprising ability to distribute pressures with minimal encumbrance around the subject, embodiments of the invention are also able to reduce skin interface pressures and, hence, can also be used secondarily to prevent diseases and disorders caused by prolonged or excessive skin interface pressures. The distribution of pressure may also reduce skin interface pressures on areas of the soft tissue where compressive forces are otherwise concentrated and, hence, tend to cause partial or complete capillary collapse. Such capillary collapse may lead to pressure ulcers, pressure sores, skin breakdown, decubitus ulcers, or other pathophysiologic conditions. The force-distributing apparatus may thus be prophylactically affixed to the human in a manner to distribute pressure in an at-risk area to prevent such pathophysiology.

Beyond prevention, in the event that initial cranial molding or skin breakdown is observed, preferred methods of the invention prompt caregivers to interventionally secure the force-distributing cranial support in a corresponding position on the subject's head, both to help in treatment of the deformation or skin breakdown, as well as to prevent further harm. The treatment aspects are enabled by the ability of the force-distributing cranial support to distribute external cranial forces and to distribute and reduce skin interface pressures on the areas of the subject's head where compressive forces are otherwise concentrated and, hence, tend to cause partial or complete capillary collapse. By distributing and reducing as much, the force-distributing cranial support thereby helps treat and allow natural healing of tissue that has already partially deteriorated due to pressure points.

In some embodiments of the invention, a force-distributing cranial support has a concavely shaped occipital cup portion and a contiguous head strap portion shaped and sized to circumferentially envelope the head of an infant while leaving the crown and face of the head exposed. The occipital cup portion and the head strap portion each comprise a patient-oriented face configured to be proximate the skin of the head when in use and an environmental-oriented face configured to face away from the skin of the head when in use. The occipital cup portion further comprises a force-distributing assembly of one or more force-distributing elements where the force-distributing elements may be a semi-solid material or, more preferably a gel, or still more preferably a hydrogel.

The materials and dimensions of the force-distributing assembly of the force-distributing cranial support are such that when the head of the infant who is lying in a supine repose on a surface is so enveloped, the force-distributing assembly distributes the force applied at a contact point on the surface over a larger area and thus disperses the pressure associated with the weight of the infant's head. Further, the head strap portion is dimensioned and oriented to secure the occipital cup portion against the posterior aspect of the infant's head. The occipital cup portion and the head strap portion comprise a readily cleanable, hypoallergenic, biocompatible, and non-irritating material that is selectively coated with a grip-providing material. Preferably the grip-providing material is oriented on a side of the force-distributing cranial support that contacts the infant's head. In other embodiments of the invention, the force-distributing cranial support also includes a padded layer within, oriented essentially adjacent to the force-distributing assembly, both the force-distributing assembly and the padded layer assuming the concavity of the occipital cup portion.

These and many other aspects of the invention will be understood by those of skill in the art in light of any claims that are or may later be associated with this patent application, especially when contemplated in light of various embodiments of the invention that are illustrated in the accompanying drawings and are further described on the following pages of this application, as well as the many other embodiments that could now or in the future also fall within the scope of those claims.

BRIEF DESCRIPTION OF THE SEVERAL VIEWS OF THE DRAWINGS

FIG. 1 shows a perspective view of a force-distributing cranial support 100, which is representative of preferred embodiments constructed according to the teachings of the present invention, and which is formed to fit on a head 210 (shown in phantom lines) of a prematurely-born neonatal subject 200;

FIG. 2 shows a further perspective view of a representative preferred embodiment of the force-distributing cranial support 100 of FIG. 1, although FIG. 2 shows the support 100 laid flat in an opened state, not fitted to the head of the subject;

DETAILED DESCRIPTION OF PREFERRED EMBODIMENTS

Figure 3:
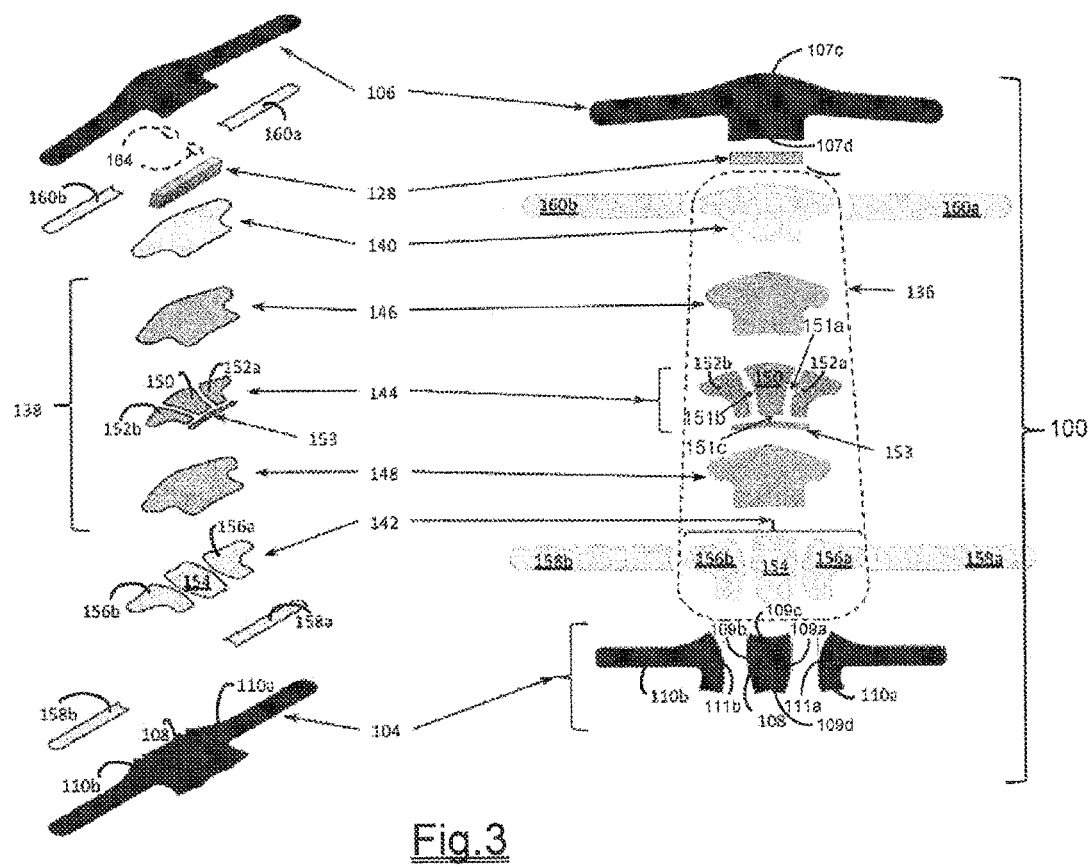
FIG. 3 shows an exploded diagram of many of the various layers and other elements that are united during manufacture to form the force-distributing cranial support 100 of FIG. 1.

A good understanding of the broader aspects of the present invention can be gleaned from consideration of several of the presently preferred embodiments that are depicted in and described with reference to FIGS. 1-10 of the drawings, where like numerals are used for like elements in the various embodiments. Occasional paragraph or section headings have been used for ease of reference, but such headings generally should not be read as affecting the meaning of the descriptions included in those paragraphs/sections.

Referring to FIG. 1, in various preferred embodiments, a force-distributing cranial support 100 is shaped and adapted to conform to a subject's head 210 in an orientation as generally illustrated in FIG. 1, which is referred to as the "operative position" of force-distributing cranial support 100. As will be evident to those of skill in the art, particularly after contemplating the further descriptions of this specification, force-distributing cranial support 100 is especially adapted to protect the head 210 of a prematurely-born neonatal subject 200 against cranial molding and other complications.

The force-distributing cranial support 100 generally has an environmental oriented face 104 and a patient oriented face 106, which provide the outer surfaces surrounding a multi-layered cushion assembly 136, which preferably includes a gel assembly 138 as described further herein. In some embodiments, the environmental oriented face 104 further comprises a medial environmental-face component 108 and two lateral environmental-face components 110a and 110b (the latter being numbered in FIG. 3). The patient oriented face 106 is oriented opposite the environmental oriented face 104. The force-distributing cranial support 100 further comprises a cephalic edge 112 and a caudal edge 114, which in use orients the cephalic edge 112 towards a crown 211 of the subject's head 210 and the caudal edge 114 towards a neck 116 of the subject.

In part to help distribute forces encountered by the occipital region 212 of the head 210 of the subject 200 when the subject is lying supinely in a neonatal bassinet or neonatal incubator, the force-distributing cranial support 100 comprises an occipital cup portion 118, which in use is snugly positioned proximate the occipital bone in the occipital region 212 of the subject's head 210.

The force-distributing cranial support 100 also has a head strap portion 120, which preferably is formed by one or more integral portions of the force-distributing cranial support 100. The structure, shapes and configuration of the head strap portion 120 are such that, while the occipital cup 118 is snugly positioned in its operative position on the occipital region 212 of head 210, head strap portion 120 provides a circumferential closure around the forehead 214 of subject 210, thereby snugly enveloping the forehead 214, while also serving to further secure both the occipital cup 118 and the overall support 100 in their respective operative positions. Head strap portion 120 preferably includes conventional releasable closure adaptations such that portion 120 provides a releasable circumferential closure around the forehead 214 of subject 210, to secure both the occipital cup 118 and the overall support 100 in their respective operative positions.

In use, the force-distributing cranial support 100 adopts a three-dimensional structure that is essentially symmetrical about a vertical plane extending between the furthest points of the occipital cup portion 118 and the head strap portion 120, the vertical plane defining a first side and a second side of the force-distributing cranial support 100.

The occipital cup portion 118 may further comprise caudal tabs 122 bilaterally extending along the caudal edge 114 of a first side and a second side of the force-distributing cranial support 100, thus oriented proximate a jaw of the subject's head 210. The head strap portion 120 may further comprise a first wing 124a and a second wing 124b, the first wing 124a and the second wing 124b extending from the occipital cup portion 118 along the cephalic edge 112. The first wing 124a and the second wing 124b are releasably attachable, preferably carrying a hook and loop fastener material to provide a secure releasable attachment, together the releasably attached first and second wings 124a and 124b form the head strap portion 120. However, any suitable fastening mechanism such as snaps, for example, could be used instead. In other embodiments, the head strap portion 120 may include a band affixed to the occipital cup portion 118 proximate the cephalic edge 112. The band and the occipital cup portion 118 may each carry a releasable attachment mechanism, for example a hook and loop fastener material between the occipital cup portion 118 and the head strap portion 120. The head strap portion 120 may further comprise an elastic material to provide a compression force sufficient to maintain the force-distributing cranial support 100 on the subject's head 210.

Referring now to FIGS. 1 and 2, the occipital cup portion 118 may further comprise ear-accommodating arches 126 defined on one side by the caudal tabs 122 and on the other side by a lower aspect of the wings 124a and 124b. In use, the force-distributing cranial support 100 is positioned in its operative position on the head 210 of the subject, in an orientation such that the ear-accommodating arches 126 are proximate the posterior aspects of the ears 219a and 219b of the subject. In such operative position, the force-distributing cranial support 100 is positioned for distributing forces that would otherwise be encountered by the occipital region 212 of the head 210 of the subject 200 when the subject is conventionally lying in a supine position on a neonatal bassinet and/or neonatal incubator.

Referring now to FIG. 2, in one embodiment, the occipital cup portion 118 may comprise a caudal rim member 128 oriented essentially proximate the caudal edge 114 and positioned under the patient oriented face 106. So oriented, when in use, the caudal rim member 128 protrudes towards the subject's head 210 and below an occipital protuberance of the subject's head 210. The caudal rim member 128 is positioned and oriented relative to the occipital protuberance to resist migration of the force-distributing cranial support 100 off the subject's head 210 during ordinary movement. The caudal rim member 128 is preferably an elongated polyethylene foam element oriented between the patient oriented face 106 and the environmental oriented face 104, however, the caudal rim member 128 may also be any other foam or gel element or any other malleable bolster material. In dimension, the caudal rim member 128 is preferably essentially the width of the occipital cup portion 118 along the caudal edge 114 thereof, although the caudal rim member 128 may also be as narrow as about 2 cm, centered along the caudal edge 114 to the same effect. The extent to which the caudal rim member 128 protrudes from the patient oriented face 106 is preferably between about 0.2 cm and about 1 cm although in some circumstances this distance may be as large as about 1.5 cm.

In other embodiments (not shown), the occipital cup portion 118 may also comprise two ridge members secured to the environmental oriented face 104. The two ridge members are preferably elastic foam or foam-filled structures that protrude outwardly to serve as mini-bolsters to aid in positioning of the subject's head 210. The two ridge members are dimensioned and positioned to provide stability to the subject's head, resisting a rolling motion. In an embodiment, the two ridge members are located essentially on opposite sides of line L, oriented approximately parallel to line L and between about 1 cm and about 3 cm from line L. In other embodiments, the two ridge members are removably affixable to the environmental oriented face 104 with a hook and loop securement mechanism, configured to allow repositioning of the two ridge members to different positions on the environmental oriented face 104 to stabilize the subject's head 210 in a variety of positions as dictated or suggested by clinical care.

Referring now to FIG. 1 and FIG. 2, an embodiment of the force-distributing cranial support 100 is shown. A flexible piping 130 extends essentially around the perimeter of the force-distributing cranial support 100 secured to both the environmental oriented face 104 and the patient oriented face 106, or to a seam therebetween. The piping 130 may further comprise a cord or a foam rod- or tube-like structure and an elongated band of flexible fabric material. Although various piping techniques could be suitable, the band of flexible fabric material is preferably turned to define a general piping shape, and its longitudinal edges are preferably folded-under along its length, to provide opposite longitudinal edges for providing a felled seam, one along each of its longitudinal edges. As is conventional for piping, one such felled seam of the elongate fabric material may be sewn or otherwise joined around the perimeter of the patient oriented face 106, and the other such felled seam may be sewn or otherwise joined around the perimeter of the environmental face 104, and the cord or foam structure is then held within the turned band of material.

In other embodiments, the piping 130 extends essentially around the perimeter of the force-distributing cranial support 100 with the exception of the most distal portion of the first and second wings 124a and 124b, for instance, leaving the distal most one to five centimeters without any piping. This may allow the distal tip of each of the first and second wings 124a and 124b to taper to a thinner dimension than the rest of wings 124a and 124b, which in turn helps accommodate overlap of such distal tips as well as the incorporation of hook-and-loop or other releasable closure connections in such distal tips in order to render the tips releasably connectable to one another.

Referring now to FIG. 2, an embodiment of the force-distributing cranial support 100 is shown in an opened state and portraying the patient oriented face 106. A cephalic edge arch 132 is essentially centered on the force-distributing cranial support 100 along the cephalic edge 112. Similarly, a caudal edge arch 134 is oriented essentially in the center of the force-distributing cranial support 100 along the caudal edge 114.

Referring now to FIG. 3, an exploded view of a preferred embodiment of the invention is shown. The force-distributing cranial support 100 is fabricated from a plurality of layers that provide for novel shaping and force-distribution and pressure reduction characteristics. A cushion assembly 136 is oriented between the environmental oriented face 104 and the patient oriented face 106 within the occipital cup portion 118, the cushion assembly 136 preferably includes a gel assembly 138 cushioned with one or more pad layers. In other embodiments, the gel layer 144 comprises one or more cushion elements. In some embodiments, the cushion assembly 136 is a force-distributing assembly. Preferably, the gel assembly 138 is sandwiched between an inner pad layer 140 and an outer pad layer 142. In one embodiment, the gel assembly 138 comprises a gel layer 144 encapsulated between an inner envelope layer 146 and an outer envelope layer 148. In some preferred embodiments, the gel layer 144 further comprises a medial gel element 150, two lateral gel elements 152a and 152b, and an inferior gel element 153 or caudal gel element 153. In some embodiments, the medial gel element 150, the two lateral gel elements 152a and 152b, and the inferior gel element 153 are each a semi-solid material.

The inner envelope layer 146 and the outer envelope layer 148 may be sealed about a perimeter so as to encase the medial gel element 150, the two lateral gel elements 152a and 152b, and the inferior gel element 153. The inner envelope layer 146 and the outer envelope layer 148 may also be sealed or partially sealed between the medial gel element 150, the two lateral gel elements 152a and 152b, and the inferior gel element 153, such sealing serving to fix each gel element 150, 152a, 152b, and 153 in its proper position during use, while also serving to isolate or separate each of the gel elements 150, 152a, 152b, and 153 from one another. The sealing may be accomplished through a heat-sealing process, a welding process, an application of an adhesive, or any other suitable process or mechanism. These seals generate seams between the various components. The seams provide a flexible bend region to facilitate the assembly of the force-distributing cranial support 100.

In one embodiment, the inner pad layer 140 is positioned essentially parallel and proximate both the gel assembly 138 and the patient oriented face 106. The outer pad layer 142 may be positioned essentially parallel and proximate both the gel assembly 138 and the environmental oriented face 104. The inner pad layer 140 may be adhered to the patient oriented face 106 with an adhesive, and the outer pad layer 142 may be adhered to the environmental oriented face 104 with an adhesive, the adhesive preferably being an acrylic adhesive. Preferably, the outer pad layer 142 may further comprise a medial outer pad element 154, two lateral pad elements 156a and 156b. The outer pad layer 142 may also be laterally flanked by two outer wing pad elements, 158a and 158b. Similarly, the inner pad layer 140 may be laterally flanked by two inner wing pad elements 160a and 160b. The four wing pad elements 158a, 158b, 160a, and 160b are positioned thus lateral to the gel assembly 138 and positioned in the first wing 124a and the second wing 124b of the force-distributing cranial support 100 between the environmental oriented face 104 and the patient oriented face 106. The two inner pad wing elements 160a and 160b and the two outer pad wing elements 158a and 158b may be adhered to the appropriate proximate first wing 124a and second wing 124b with an acrylic adhesive or other suitable affixing agent. In other embodiments, two inner pad wing elements 160a and 160b and the two outer pad wing elements 158a and 158b may be adhered to the gel assembly 138 with an acrylic adhesive or other suitable affixing agent.

The environmental oriented face 104 and the patient oriented face 106 may be the same type of material or may be different. Both faces 104 and 106 may comprise a flexible textile that is preferably capable of stretching to conform to an externally applied force which can, thus, minimize or even prevent an accompanying increase in interface pressure. The textile may also recover from such aforementioned stretch, returning to its original condition and shape. In some preferred embodiments, the textile is configured to have a low friction surface that reduces shear when laterally shifted in relation to an interfacing surface. In some preferred embodiments, the textile is hypoallergenic, biocompatible, and non-irritating. By way of a non-limiting example, the textile may be Recovery 5™ Healthcare Fabric or preferably Recovery 5™ HF Healthcare Fabric (Staftex Textiles Limited, Toronto, Canada).

The textile of faces 104 and 106 may also permit water vapor transfer to facilitate the movement of perspiration from the human subject to and preferably through one or more of the plurality of layers of the force-distributing cranial support 100 and may be configured for moisture vapor transfer between about 200 gr/m2/24 hrs to about 900 gr/m2/24 hrs. By way of a non-limiting example, the textile may be Estane® 58245 (Lubrizol, Cleveland, Ohio, USA). The textile may also comprise a combination of these stretch and moisture vapor transfer characteristics in one or more segments.

The textile of faces 104 and 106 may further comprise an antimicrobial agent or may have antimicrobial properties. The antimicrobial agent may be Ultra-Fresh DW-30® (Thomson Research Associates, Toronto, Canada) although many other biocompatible antimicrobial agents may be suitable also.

In some embodiments, the force-distributing cranial support 100 further comprises a grip-providing substance 162 or gripping material affixed to the patient oriented face 106 and oriented proximate the subject's head 210 when in use. The grip-providing substance 162 may cover the entire patient oriented face 106, or the grip-providing substance 162 may be configured in a pattern, covering only a portion of the patient oriented face 106. The pattern of the grip-providing substance 162 may be one or more stripes, one or more ellipses, one or more regular polygons, one or more dots, one or more lines essentially parallel to or perpendicular to the cephalic edge 112, other shapes, or a combination of any of these. The grip-providing substance 162 may be generally oriented on the occipital cup portion 118, generally on the head strap portion 120, or on both. In some preferred embodiments, the grip-providing substance 162 is oriented both along a portion of the patient oriented face 106 of the head strap portion 120, in a pattern on the occipital cup portion 118, and over the caudal rim member 128. In some embodiments, the pattern of the grip-providing substance 162 on the occipital cup portion 118 assumes the shape of an ellipsis or a polygon oriented essentially around the center of the occipital cup portion 118 while leaving the center of the occipital cup portion 118 uncovered by the grip-providing substance 162.

In an illustrative embodiment, the grip-providing substance 162 so applied to the occipital cup portion 118 may help minimize movement of the force-distributing cranial support 100 when affixed to the subject's head 210. The grip-providing substance 162 in some preferred embodiments comprises a cured silicone such as Bluestar TCS 7536 Silicone (Bluestar Silicones, East Brunswick, N.J., USA). In other embodiments, the grip-providing substance 162 may comprise Mediderm 3200 or Mediderm 4000 (Mylan Technologies, St. Albans, Vt.), although other grip-providing materials such as polysiloxane may also be used. In some embodiments, the grip-providing substance 162 has a thickness between about 10 microns and about 10 millimeters, preferably between about 50 microns and about 250 microns.

The inner pad layer 140 and the outer pad layer 142 may each comprise a polyethylene foam known to be medical grade and hypoallergenic. In other embodiments, the inner pad layer 140 and the outer pad layer 142 may each comprise a polyurethane foam known to be medical grade and hypoallergenic. By way of a non-limiting example, the polyethylene foam may be MDFT3500 (CCT Tapes, Philadelphia, Pa., USA) although other foam material may be used in other embodiments. In other embodiments, the polyethylene foam may be TM-6563 (MacTac, Stow, Ohio, USA). The polyethylene foam may be coated on one or both sides with an adhesive such as an acrylic adhesive. In some embodiments, the inner pad layer 140 and the outer pad layer 142 are dimensioned less than about 10 millimeters, more preferably less than about 5 millimeters and more preferably about 1 millimeter in thickness. The thickness dimensioning of the inner pad layer 140 and the outer pad layer 142 provides sufficient flexibility to allow the force-distributing cranial support 100 to follow the contours of the subject's head 210.

In one embodiment the gel elements 150, 152a, 152b, and 153 of the gel layer 144 are comprised of a hydrogel. The hydrogel may contain between about 10% and about 99.9% water, preferably between about 15% and about 70% water, and more preferably between about 35% and about 50% water. More preferably still, the water content of the hydrogel is about 40%. The gel layer 144 may be a proprietary hydrogel KM501 from Katecho, Inc. (Katecho, Des Moines, Iowa, USA). The hydrogel provides a semi-solid viscoelastic gel material that is resistant to flow or oozing and yet, surprisingly, provides a soft resilience to compression from an externally applied force and simultaneously provides a distribution of that externally applied pressure. The gel layer 144 is relatively thin, being dimensioned to have a thickness between about 2 mm and 20 mm, or preferably between about 4 mm and about 15 mm, or more preferably still between about 6 mm and about 10 mm.

The inner envelope layer 146 and the outer envelope layer 148 may each comprise a thermoplastic elastomer, preferably configured as pliable and having an ability to be stretched without becoming deformed. Preferably, the thermoplastic elastomer possesses a moisture vapor transfer rate (MVTR) below about 15 grams per square meter per day such that the hydrogel contained therein will be less inclined to lose water concentration due to evaporation. The thermoplastic elastomer may be a thermoplastic elastomer alloy such as Versaflex™ CL2250 (PolyOne, McHenry, Ill., USA)

and may be dimensioned between about 0.5 mm and 5 mm in thickness, preferably about 0.8 mm in thickness.

In other embodiments, a desiccant is contained within the force-distributing cranial support 100, preferably within the pad layer 140 or inner envelope layer 146, such desiccant is preferably adapted to absorb moisture from the subject that passes through the patient oriented face 106. As alternatives, the desiccant may be oriented with the inner pad layer 140, the outer pad layer 142, or as a powder or pellets situated between any of the plurality of layers of the force-distributing cranial support 100. So positioned, the desiccant may provide a moisture gradient from the subject to the force-distributing cranial support 100 to promote the transmission of moisture away from the subject. Other powered or non-powered means may also be substituted for, or used in conjunction with such desiccant to enhance the moisture gradient.

In other embodiments, the gel assembly 138 further comprises one or more regions wherein the inner envelope layer 146 and the outer envelope layer 148 are adhered or bonded together selectively, for instance by welding, in one or more regions to limit the effective thickness of the gel assembly 138 in that region thus preventing the gel layer 142 moving through or existing in the one or more regions. These one or more regions may be linear, circular, curvilinear, or any polygon in shape. In use, these one or more regions may limit the movement of the gel layer 142 within the gel assembly 138 in a manner so as to maintain gel throughout the gel assembly 138 even as an external force is applied locally thereon.

The force dispersing properties and the concave curvature of the occipital cup portion 118 are facilitated by the interacting shapes of each gel element 148, 152*a*, 152*b*, and 153, each outer pad layer element 154, 156*a*, and 156*b*, and each environment-face component 108, 110*a*, and 110*b*, which shapes are characterized in part by their various edges. The edges of the medial outer pad element 154 facing the two outer lateral pad elements 156*a* and 156*b* are essentially shaped as an obtuse angle. Similarly, the edges of each of the two lateral environmental-face components 110*a* and 110*b* facing the medial environmental-face component 108 are shaped as obtuse angles also.

Referring again to FIG. 1, the shape and other characteristics of the occipital cup 118 and wings 128*a*, 128*b* of force-distributing cranial support 100 allow the support 100 to be operatively positioned on the subject's head 210 in a way that distributes forces that would otherwise risk cranial molding, while simultaneously allowing open access to various key surfaces of the subject's head 210. Particularly, the force-distributing cranial support 100 has an inherent three-dimensional characteristic suited to circumferentially envelope or wrap around the head 210 of the subject 200 while preferably leaving the crown 211 of the subject's head 210 exposed for therapeutic or diagnostic access. As will also be appreciated from the operative position illustrated in FIG. 1, the preferred operative position of force-distributing cranial support 100 also leaves the subject's face 215, frontal neck 225, and ears 219*a* and 219*b* unobstructed. Hence, the subject 200 retains its natural abilities to use its hearing and vision senses, as well as its nose 217 and mouth 218, substantially unimpeded despite having force-distributing cranial support 100 secured in its operative position on head 200. To effectively distribute force externally applied to the subject's head 210, the force-distributing cranial support 100 will ideally be essentially in contact therewith. However, the environmental oriented face 104, the patient oriented face 106, the gel assembly 138, inner pad layer 140, and the outer pad layer 142 are all essentially flat, having no inherent concavity in preferred embodiments. Despite such lack of inherent concavity, the combined shapes, construction, and materials uniquely combine to promote a concave structure.

Referring again to FIG. 3, it was surprisingly found that by shaping the opposing edges of medial environmental-face component element 108 and the lateral environmental-face components 110*a* and 110*b* as obtuse angles, that when stitched together transform the individual two-dimensional elements into a three-dimensional concave form. Further, by matching the shapes and angles of the medial environmental-face component element 108 and the lateral environmental-face components 110*a* and 110*b* with the medial outer pad element 154 and the lateral outer pad elements 156*a* and 156*b*, the outer pad layer 142 can then be affixed to the concave shape of the environmental oriented face 104 maintaining this shape. Most surprisingly, it was also found that the gel assembly 138 with the gel elements 150, 152*a*, and 152*b* could be forcibly affixed to the concave shape of the outer pad layer 142, with the flexible seams between the gel elements 150, 152*a*, and 152*b* providing sufficient conformability because of the particular shapes of the seams and of the gel elements 150, 152*a*, 152*b*, and 153. In another embodiment, it was found that that the gel assembly 138 with the gel elements 150, 152*a*, and 152*b* could be forcibly affixed directly to the concave shape of the environmental face 104, aligning the flexible seams between the medial gel element 150 and the first and second lateral gel elements 152*a* and 152*b* with the shapes and angles of the medial environmental-face component element 108 and the lateral environmental-face components 110*a* and 110*b*, thus resulting in the gel assembly 138 adopting the concavity of the so assembled environmental face 104.

The radius of the resulting concavity is such that the occipital cup portion 118 conforms to the convex shape of the subject's head 210, tucking under the occipital protuberance. It was also found that generating concavity from the two-dimensional materials of the force-distributing cranial support 100 was further promoted by dimensioning the height along line L of the environmental oriented face 104 and the patient oriented face 106 slightly differently. Specifically and surprisingly, dimensioning the height of the patient oriented face 106 between only about 2 mm to 5 mm less than the height of the environmental oriented face 104 contributed to a cupping effect when the two faces 104 and 106 are joined in construction.

In the gel layer 144, the medial gel element 150 may be between about 2 cm and about 8 cm at its widest dimension and between about 1 cm and about 4 cm at its narrowest dimension. The distance separating the medial gel element 150 and each of the lateral gel elements 152*a* and 152*b* is between about 0.2 cm and about 1 cm, approximately equidistant along a curved path. The overall width of each of the lateral gel elements 152*a* and 152*b* is between about 2 cm and about 10 cm. The encapsulated inferior gel element 153 follows a curve defined by the base of the medial gel element 150 and the two lateral gel elements 152*a* and 152*b*, separated by between about 0.2 cm and about 1 cm and extending in width between about 2 cm and about 10 cm. Orthogonal to the width of the medial gel element 150, the height of the medial gel element 150 is between about 2.5 cm and about 10 cm. When combined with the separation between the medial gel element and the encapsulated gel element of the inferior gel element 153, the height of the collection of gel elements 150, 152*a*, 152*b*, and 153 of the gel layer 144 is between about 4 cm and about 11 cm.

Another component of the gel assembly 138, the inner pad layer 140 is dimensioned with a similar aspect ratio to the gel assembly 138, scaled between about 110% and about 50% of the gel assembly 138, preferably between about 85% and about 75%. The medial outer pad element 154 is shaped similarly to the medial gel element 150 and is dimensioned between about 90% and about 120% of the medial gel element 150.

In some embodiments, taken together, the force-distributing cranial support 100 is dimensioned to fit a head. In some preferred embodiments, the force-distributing cranial support 100 is dimensioned to fit the head of an infant. To facilitate proper sizing to a range of infants from premature to toddler, the force-distributing cranial support 100 may be constructed in multiple sizes, for instance a small, a medium, and a large unit. By way of an illustrative example, the small size may be dimensioned to fit the head of an infant with a circumference at the widest plane from about 23 cm to about 30 cm, the medium from about 28 cm to about 33 cm, and the large from about 33 cm to about 38 cm. To provide for this, given sufficient overlap of the first and second wings 124a and 124b, in one preferred embodiment the tip-to-tip measurement of the patient oriented face 106 as shown in FIG. 2 may be about 34 cm for the small size, about 41 cm for the medium size, and about 48 cm for the large size. The height of the force-distributing cranial support 100 along line L of FIG. 2 from the caudal edge 114 to the cephalic edge 112, in some preferred embodiments, is about 60 mm for the small size, about 76 mm for the medium size, and about 90 mm for the large size. The width of the occipital cup portion 118, as defined by the edge-to-edge measurement at the bilateral ear accommodating arches 132, in an embodiment is about 7 cm for the small size, about 10 cm for the medium size, and about 15 cm for the large size. It is understood that to accommodate heads of other sizes, that appropriately proportioned dimensions could be readily used for the force-distributing cranial support 100 without deviating from the invention.

As noted in the description of the composition of the gel layer 144 previously, the gel layer 144 is thin. When combined with the other components of the cushion assembly 136, the cushion assembly 136 is also thin. The inner pad layer 140 and the outer pad elements 154, 156a, and 156b may have an uncompressed thickness of between about 0.5 mm and about 5 mm, preferably between about 1 mm and about 2 mm. Thus the combined thickness of the cushion assembly 136 is between about 3 mm and about 30 mm, preferably between about 6 mm and about 14 mm and the overall thickness of the force-distributing cranial support 100 at the occipital cup portion 118 is between about 5 mm and about 32 mm, preferably between about 8 mm and about 16 mm.

In other embodiments, the gel assembly 138 is adhered directly to the patient oriented face 106 in a manner than brings together the opposing edges of each notch caused the gel assembly 138 to cup into a concave shape. The outer pad layer 142 may be adhered to the gel assembly 138 in an essentially overlapping position and may also be adhered to the environmental oriented face 104.

In some embodiments, the cup-like combination of the gel assembly 138, in the inner pad layer 140, and the outer pad layer 142 are positioned between the patient oriented face 106 and the environmental oriented face 104, the environmental oriented face 104 comprising the medial environmental-face component 108 and the lateral environmental-face components 110a and 110b. In this manner, the patient oriented face 106 provides a continuous uninterrupted surface, without seams, folds, overlaps, or any other discontinuities, to the subject's head 210 when deployed thereby minimizing pressure concentrations on the skin of the subject's head 210.

As can be seen in FIG. 3, the medial edges 111a and 111b of the two lateral environmental-face components 110a and 110b, respectively, and the lateral edges 109a and 109b of the medial environmental-face component 108 are all preferably curvilinear and convex relative to their respective component panels 110a, 110b and 108 of environmental surface 104. Despite such convexly curvilinear nature, during fabrication of force-distributing cranial support 100, opposite ones of these convexly curvilinear edges 109a-b and 111a-b are essentially opposed to one another such that, if laid flat, they curve in opposite directions from one another. So positioned and shaped, the medial environmental-face component 108 and the lateral environmental-face components 110a and 110b are affixed along their facing edges 110a-b and 111a-b, for instance via sewing, in a manner such that the medial edge of each lateral environmental-face components 110a and 110b is affixed to the lateral edge of the medial environmental-face component 108. More specifically, the convexly curvilinear course of medial edge 111a is assembled and joined to align with the oppositely-curved lateral edge 109a. Likewise, medial edge 111b is assembled and joined to align with the oppositely-curved lateral edge 109a. As a result, in a seemingly incongruous manner, their respective curvilinear courses are assembled and permanently joined to align with one another despite their opposite curvature, to unite panels 108, 110a and 110b to form a unitary environmental face 104. The result also produces a three-dimensional contour for environmental face 104, which in turn creates a predisposition to flex various other layers of force-distributing cranial support 100 to thereby form the contour of occipital cup 118 in a manner that tends to conform with the occipital region 212 of a neonatal subject's head 210. In addition to the incongruous joinder of oppositely curved edges that form internal seams within environmental oriented face 104, cephalic edge 114 of force distributing cranial support 100 is also formed by the union of oppositely curved edges 109c and 107c. More particularly, the cephalic edge 109c of the medial environmental panel 108 is concavely curved in the cephalic direction while the mating cephalic edge 107c of patient oriented face 106 is convexly curved in the cephalic direction. Again, despite such opposite curvatures, edges 109c and 107c are flexed into alignment and sewn together during fabrication of force-distributing cranial support 100. Such incongruous joinder to form cephalic edge 114 further contributes to ensuring the three-dimensional concavity of occipital cup 118, as do other incongruous joinders within the construction of force-distributing cranial support 100.

The curves of the medial environmental-face component 108 and the lateral environmental-face components 110a and 110b are shaped and positioned in such a manner as to provide a similar amount of concavity as the cup-like combination of the gel assembly 138, the inner pad layer 140, and the outer pad layer 142. The piping 130 affixed, for instance via sewing, around the perimeter of both the environmental oriented face 104 and the patient oriented face 106, securing the plurality of layers therewithin. In other embodiments, the environmental oriented face 104 and the patient oriented face 106 are sown around the perimeter of both, effecting the assembly of the force-distributing cranial support 100.

When so placed on an infant, the force distribution apparatus, because of its particular features and characteristics, distributes external forces away from the area of contact between the tissue and an external surface as a smaller force over a larger area. Without being limited to any particular theory, this distribution of pressure may reduce skin interface pressures on areas of the soft tissue where compressive forces are otherwise concentrated and, hence, tend to cause partial or complete capillary collapse. Such capillary collapse may lead to pressure ulcers, pressure sores, skin breakdown, decubitus ulcers, or other pathophysiologic conditions. The force distribution apparatus may thus be prophylactically affixed to the human in a manner to reduce pressure in an at-risk area to prevent such pathophysiology.

When affixed to the head of the infant, the force-distributing cranial support 100 is configured to reduce compressive forces on soft, flexible cranial plates that define a cranial cavity. The force-distributing cranial support cradles the head, further promoting the proper development of the infant's head, reducing the incidence, preventing, or treating the development of plagiocephaly, brachycephaly, and dolichocephaly (referred to collectively as, "positional cranial molding" or, simply, "cranial molding"). The reduction of the development of cranial molding may permit the normal growth of brain tissue within the cranial cavity, perhaps positively affecting cognitive developmental. In use, the force-distributing cranial support 100 can be applied to the head of a prematurely born infant, born less than 36 weeks gestational age (otherwise known as menstrual age), a full-term infant, a toddler, or any age in between. The force-distributing cranial support 100 can be applied at any time but is especially useful when the infant is lying in a supine position.

Irrespective of the particular purpose for using the force-distributing cranial support 100, its purpose is achieved by orienting and circumferentially securing the force-distributing cranial support 100 in place. To do so, referring again to FIG. 1, the force-distributing cranial support 100 is placed on the subject's head 210, and the first and second wings 124a, 124b are releasably affixed together to close the head strap portion 120 snugly or securely over the forehead 214 of the subject 200. As the first and second wings 124a, 124b come together, the force-distributing cranial support 100 achieves a deployed shape that is essentially elliptical as viewed from the cephalic—caudal projection. Surprisingly, the caudal edge arch 134 results in an essentially flat caudal edge 114 and the cephalic edge arch 132 results in an essentially flat cephalic edge 112 when so deployed.

In other embodiments, a thermal retention cap is removably attached to the force-distributing cranial support 100 with a fastening system. The fastening system may be positioned along the perimeter of the thermal retention cap and proximate the cephalic edge 112 and may comprise a hook and loop apparatus, magnets of opposite polarity, a tongue-and-groove mechanism, or any other system capable of removable attachment. A patient-facing surface of the thermal retention cap may be comprised of the textile of the force-distributing cranial support 100 and may be constructed of the same plurality of layers as the force-distributing cranial support 100. In other embodiments, the thermal retention cap may comprise an insulation material configured to retain heat from the subject's head near the subject rather than escaping to the environment. This may provide a therapeutic benefit to the subject, especially when the subject is an infant due to the poor inherent thermal regulation abilities of infants. In addition, the thermal retention cap may also be used in conjunction with a hypothermia-inducing fluid-filled headgear system in a manner to prevent environmental thermal conditions from influencing the cool therapeutic temperature of the headgear system.

Figure 4:
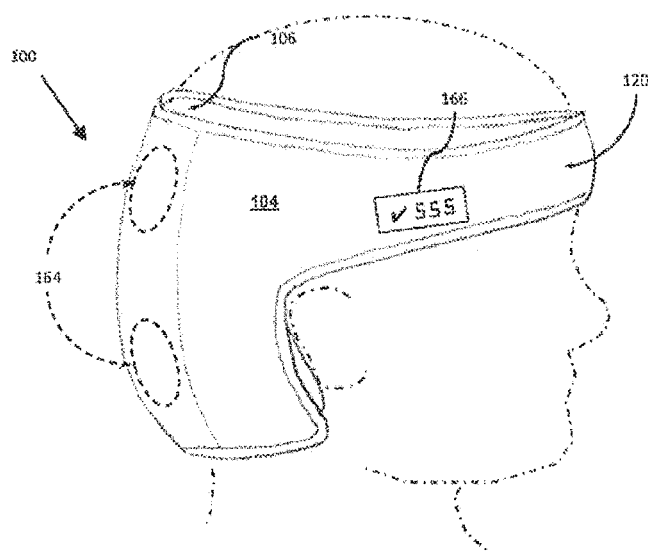
FIG. 4 shows a perspective view of a variation of force-distributing cranial support 100 in its operative orientation on neonatal head 210 much as in FIG. 1, while FIG. 2 further illustrates the incorporation of pressure sensors 164 (shown in hidden line) and an associated display 166 to enable feature enhancements not illustrated in FIG. 1.

Referring to FIG. 4, another preferred embodiment is shown, where the force-distributing cranial support 100 further comprises a sensor 164 and a processing unit (not shown). When the force-distributing cranial support 100 is deployed on a subject's head 210, the proximity of the force-distributing cranial support 100 to the subject's head 210 affords the opportunity to sense physical and physiologic variables associated with the use of the force-distributing cranial support 100 or the condition of the subject. The processing unit is in data communication with the sensor 164 and may be configured to transform data from the sensor 164 for a display 166 with which it is in data communication, for transmission to another device or system, or both. The display 166 may be a flexible liquid crystal display (LCD) affixed to the force-distributing cranial support 100. The physical and physiologic variables may be transmitted from the processing unit to the display 166 to provide clinical information for the user caring for the subject. The physical and physiologic variables may also be transmitted to a remote system such as a patient monitoring system, a remote display unit, a clinical network, a patient data management system, or similar information management system. The processing unit may also comprise a transmitting unit, configured to enable communication between the processing unit and the remote system. The transmitting unit may employ any electromagnetic mechanism for data communication. These electromagnetic mechanisms may include but are not limited to physical connection of lead wires whether digital or analog in nature, a radio-frequency transmission such as ultrahigh frequency radio waves as specified in the Bluetooth communication protocol, a radio-frequency query system such as radio-frequency identification (RFID) system, or an infrared transceiver such as specified by the Infrared Data Association (IrDA).

In some embodiments, the sensor 164 is a pressure sensor such as a strain gauge sensor adapted to detect and quantify the pressure between the subject's head and the patient oriented face 106 of the force-distributing cranial support 100. For minimal interference and readings that most closely reflect conditions at the head 210, such a pressure sensor 164 is preferably mounted within the multiple layers of force-distributing cranial support 100. For instance, as illustrated in phantom line in FIG. 3, sensor 164 is positioned between the gel layer 144 and patient oriented face 106. The processing unit is configured to transform data from the sensor 164 into a numeric value in appropriate units, for instance millimeters of mercury (mmHg), that are then shown on the display 166. In other embodiments, the processing unit compares the pressure detected by the sensor 164 with a threshold value that may be indicative of a pressure suitable for efficacious use of the force-distributing cranial support 100. When a pressure sensed exceeds the threshold value, the display 166 will so indicate. This may provide feedback to the user regarding the proper deployment of the force-distributing cranial support 100.

In other embodiments, the sensor 164 is a position-detecting sensor such as an inclinometer, a gyroscope, or an accelerometer. In some embodiments, the sensor 164 is a triple-axis gyroscope device such as an InvenSense ITG-3701 chip. In other embodiments, such a sensor 164 is a six-axis device that combines gyroscope and accelerometer functionality in the form of laser, fiber optic or solid state devices or the like that are suitable for being mountable on circuit boards, such as an InvenSense MPU-6500 chip. The sensor 164 detects the orientation of the head of the subject, for instance whether the subject is in a lying position and if so, whether the subject is laying prone, supine, or lateral. Alternately, the sensor 164 detects whether the subject is moving rapidly as my be the case if the subject is an infant and is moving in a rapid manner as would be expected during alert play or engagement with the environment. Periodically the processing unit communicates with the sensor 164, passing this orientation information from the sensor 164 to the processing unit where it is stored in memory within the processing unit. In some embodiments, the orientation information is processed within the processing unit, calculating approximate times during which the subject was asleep and awake, and for each of these states, asleep and awake, the fraction of time in a supine, a prone, and a lateral orientation. These data may be shown on display 166, appropriately labeled.

In other embodiments, such data may be communicated by the processing unit to a remote system. When these data are communicated to the remote system, the remote system may further process the fractions of time of sleep and wakefulness, of activity and repose, and of prone, supine and lateral orientation into a clinically engaging report that summarize the subject's activity and orientation. By way of an illustrative example, when the subject is an infant, report may indicate that the infant was placed in a prone position for sleep twenty-eight days of the previous month. A clinician may consider using this information to guide the parents or caregiver of the infant to encourage them to place the infant in a supine position in compliance with the American Academy of Pediatrics (AAP) Safe-To-Sleep guidelines.

In other embodiments, the sensor 164 is an infrared spectroscope oriented within the force-distributing cranial support 100 to emit light towards the subject's head 210. Depending on the amount of light of various wavelengths that is absorbed by the subject's tissue, an amount of light at various wavelengths is reflected back to the infrared spectroscope. Since the absorption is related to the blood within the tissue, the infrared spectroscope provides an indication of local blood flow and the systemic cardiac cycle. The processing unit obtains the data from the sensor 164 and may quantify local blood flow in a region of the subject's head 210, the oxygen saturation of the arterial blood in the tissue proximate the sensor 164, the heart rate of the subject, the respiration rate of the subject, or an estimate of the fluid status of the subject, for instance by calculating the pulse pressure variation. Other calculations based on an infrared spectroscope care also possible. The aforementioned physiologic variables may be collectively referred to as cardiopulmonary variables. The cardiopulmonary variables may be transmitted from the processing unit to the display 166 and may also be transmitted to a patient monitoring system, a remote display unit, a clinical network, a patient data management system, or similar information management system.

In still other embodiments, the sensor 164 is an ultrasonic transceiver oriented to insonify the subject's head 210, often through a fontanel with ultrasound waves and to receive reflected ultrasound waves subsequently reflected from structures therewithin. The ultrasound transceiver is adapted to transmit and received wavelengths between about 20 KHz and about 1 GHz and more preferably between about 1 MHz and 20 MHz. The processing unit in data communication with the sensor 164 is configured to analyze Doppler shifts in a received signal to assess cranial anatomy, physiology, or pathophysiology. By way of non-limiting examples, this includes intracranial pressure, cranial cavity volume measurements, cerebral blood flow, cerebral blood volume, carotid artery occlusions, ventricle volume measurements, and parenchymal perfusion. Such measurements and data may be transmitted by the processing unit to a remote display unit, a clinical network, a patient data management system, or similar information management system.

In other embodiments, the sensor 164 is a temperature sensor such as a thermocouple or a thermistor. The sensor 164 may be positioned proximate a portion of the subject's head 210 such as by the forehead 214 or a temporal bone. The data from the sensor 164 is processed by the processing unit and communicated via a data communication to the display 166. Tracking the subject's temperature or changes in the subject's temperature, especially when the subject is an infant known to have poor intrinsic temperature regulation capabilities, may provide useful clinical guidance. The clinical guidance may result in a clinician deploying the thermal retention cap on the force-distributing cranial support 100 or, alternately, detaching the thermal retention cap from the force-distributing cranial support 100.

In other embodiments, the sensors 164 include a tympanic temperature sensor with a sensing element (not shown) connected to a surface of the force-distributing cranial support 100 at a location over or near one of the ear-accommodating arches 126, in an orientation that is directed toward the adjacent ear 219 of the subject 200. The tympanic temperature sensor may preferably include a soft memory foam surrounding an infrared temperature sensor element or other temperature sensor element including, for instance, a thermocouple or thermistor. The infrared temperature sensor element may be a ZTP-135BS Thermopile IR Sensor (GE Measurement & Control, Billerica, Mass.). The tympanic temperature sensor may be held in place in operation with the soft memory foam that is sized to fit snugly in the ear 219 of the subject, shielding the ambient environment from the sensor element in a manner that minimizes the interference with the measurement of the temperature of the subject. Alternative embodiments and configurations for sensors usable for detecting the temperature, Sa02 or other health related conditions of subject 200 will also be understood by those of skill in the art, which may also or alternatively be incorporated in force-distributing cranial support 100 as part of sensors 164.

Figure 5:
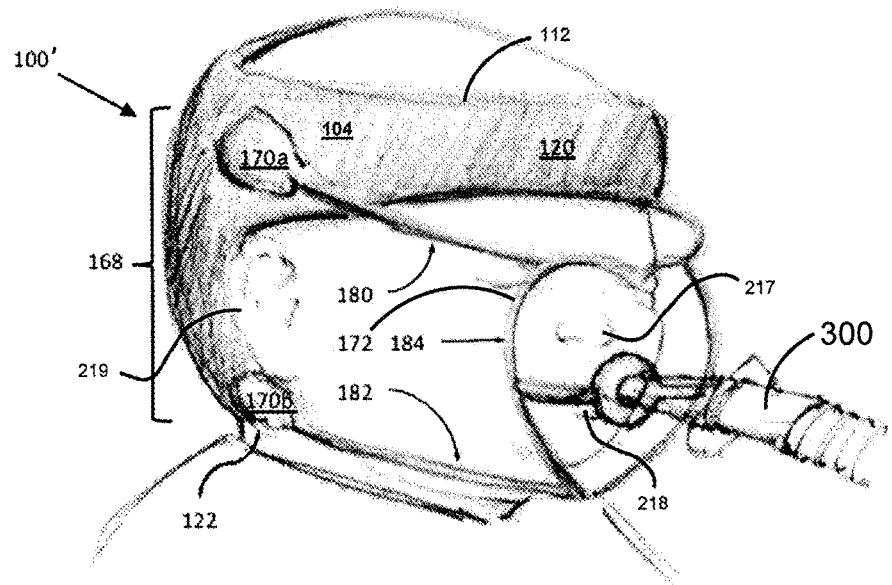
FIG. 5 shows a variation 100' of force-distributing cranial support 100 in a perspective view, as operatively oriented on the head of a neonatal subject, with particular detail to illustrate an anchor system 168 for an accessory securement system 172.

Referring now to FIG. 5, in yet another representative embodiment, an accessory-ready variation 100' of the force-distributing cranial support 100 further includes an anchor system 168 that allows for connecting and/or supporting accessories to cranial support 100'. But for the unique adaptations described here, the accessory-ready variation 100' is generally identical to the force-distributing cranial support 100 of FIGS. 1-3. In some embodiments of the accessory-ready variation 100', the anchor system 168 comprises one or more anchor apparatus 170 (FIG. 5 only showing two such apparatus 170, which are particularly designated as apparatus 170a and 170b). Each such anchor apparatus 170 are preferably securely integrated with the force-distributing cranial support 100' on its environmental surface 104. The principle purpose for anchor apparatus 170 is for connecting and supporting accessories or other objects to the force-distributing 100'. Such anchor apparatus 170 are preferably three or more in number, to provide enhanced stability for the support of accessories that may be anchored to anchor apparatus 170, particularly for supporting accessories that may contribute to the health of the subject, such as for the support of a ventilator tube 300 or the like relative to the mouth 218 of the neonatal subject 200. More particularly, anchor apparatus 170 are most preferably four in number, located on environmental surface 104 in two positions on the left side and two positions on the right side of the subject's head 210—above and below each ear 219 when force-distributing cranial support 100 is in an operative position—as illustrated by the locations of the two anchor apparatus 170 shown in FIG. 5.

Figure 6:
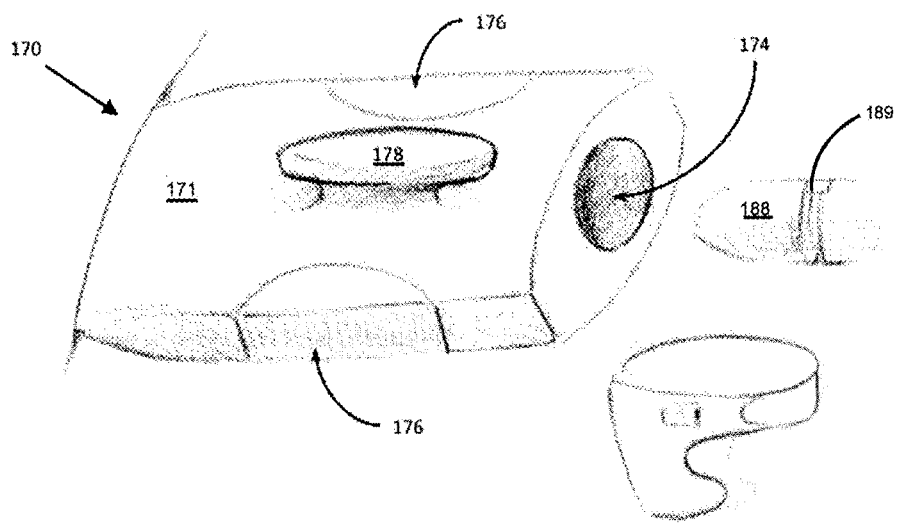
FIG. 6 shows a representative preferred embodiment of an anchor apparatus 170 in a perspective view, as part of the anchor system 168 and related components illustrated in FIG. 5.

Referring to FIG. 6 in conjunction with FIG. 5, each of the anchor apparatus 170 preferably serve their general purpose by providing anchor positions for securely connecting an accessory securement system 172. Then, once securely connected to the multiple anchor apparatus 170, the accessory securement system 172 in turn supports an accessory such as tube 300 in a suitable position for its intended operation relative to the mouth 218 of neonatal subject 200.

In some embodiments, each anchor apparatus 170 has a main body 171 that defines a primary connection point 174 for connecting objects or accessories to force-distributing cranial support 100. Each such primary connection point 174 is preferably in the form of a female receptacle 174 that is sized to receive a corresponding end 188 of the struts 180, 182 of accessory securement system 172. The main body 171 of each anchor apparatus 170 may also incorporate a spring-based latch mechanism for releasably retaining the end 188 of the corresponding strut 180, 182 that is inserted into female receptacle 174. The spring-based latch mechanism of each main body 171 is spring-biased to retain the corresponding end 188 that is fully inserted in the female receptacle 174, preferably by spring-biasing a pawl or the like to securely engage a groove 189 or other feature of the strut end 188 when it is fully inserted in receptacle 174. As is conventional for spring-biased latch mechanisms, the latch mechanism of each main body 171 may be operated to selectively release the strut end 188 by actuating finger release tabs 176 on main body 171. Preferably, tabs 176 are embodied as opposing finger release tabs 176a and 176b, which are oriented on opposite sides of each main body 171. The latch mechanisms are configured to release the strut end 188 by manually squeezing the two opposite finger release tabs 176a and 176b toward each other, in a manner such that the travel of the finger release tabs 176 is essentially perpendicular to the female receptacle 174. In some preferred embodiments, the anchor apparatus 170 further comprise a cleat 178 located an outer surface of the anchor apparatus 170 for enabling a second mode of attaching objects or accessories relative to force-distributing cranial support 100.

Referring again to FIG. 7, in the illustrated preferred embodiment, four anchor apparatus 170 include a first pair of the anchor apparatus 170a and a second pair of anchor apparatus 170b. Although the view of FIG. 7 only shows one anchor apparatus of each such pair (170a and 170b, respectively), it should be understood that each such pair includes the one as shown on the right side of the head 210, together with another similar one (not shown) on the opposite, left side of the head 210.

Each anchor apparatus 170a of the first pair is positioned proximate the cephalic edge 112 of force-distributing cranial support 100, generally either on the occipital cup portion 118 or on the head strap portion 120. That first pair of anchor apparatus 170a is referred to collectively as the cephalic anchor apparatus 170a. The female receptacle 174 of the cephalic apparatus is oriented towards the head strap portion 120. Similarly, each anchor apparatus 170b of the second pair is positioned proximate the caudal tab 122 of the respective left and right sides of the force-distributing cranial support 100. That second pair of anchor apparatus 170b is referred to collectively as the caudal anchor apparatus.

The female receptacles 174 of the caudal anchor apparatus 170b are oriented essentially parallel to the female receptacles 174 of the cephalic anchor apparatus 170b.

In some embodiments, the accessory securement system 172 comprises cephalic arch member 180, a caudal arch member 182, and a connecting member 184, the caudal arch member 182 being essentially parallel to the cephalic arch member 180 and the connecting member 184 being affixed to the cephalic arch member 180 and the caudal arch member 182. The connecting member 184 may have the shape of a shaft, an ovoid, a triangle, a plurality of shafts, a stylized heart, a polygon, or other curvilinear projection. The connecting member 184 may be essentially centered relative to the cephalic arch member 180 and the caudal arch member 182. The cephalic arch member 180, caudal arch member 182, and connecting member 184 may each comprise a material or materials that provide a semi-rigid yet resilient structure, somewhat yieldingly resisting deflection. The cephalic arch member 180, caudal arch member 182, and connecting member 184 may each be coated with a soft, wipeably cleanable, hypoallergenic material that facilitates use in a clinical environment and reduces a risk of marring, scratching, injuring, or traumatizing a subject's head 210 or the skin thereon. The cephalic arch member 180 and the caudal arch member 182 each further comprise two proximal male ends oriented at the ends opposite of a medial aspect of the arch.

A cleat 178 similar to the cleat 178 of the anchor apparatus 170 may be oriented on the cephalic arc member or the caudal arch member 182. The cephalic arch member 180 and the caudal arch member 182 may also each further comprise a length of elastic material oriented between the medial aspect of the arch and each of the two proximal male ends, the elastic material that resists stretching the medial aspect from the two proximal male ends. In use, the elastic material may help keep the accessory securement system 172 proximate the subject's head 210 even as clinically indicated devices are introduced under, in, or on the accessory securement system 172. In an alternate embodiment, the material of the cephalic arch member 180 and the caudal arch member 182 comprises an elastic property that resists stretching the medial aspect away from the two proximal male ends. The two proximal male ends of the cephalic arch member 180 and the caudal arch member 182 are shaped and sized to be insertable into the female receptacle 174 of the anchor apparatus 170. The two proximal male ends of the cephalic arch member 180 and the caudal arch member 182 may also be configured to have a mating latch mechanism for the anchor apparatus 170. In some preferred embodiments, the cephalic arch member 180 is mateable to the cephalic anchor apparatus and the caudal arch member 182 is mateable to the caudal anchor apparatus 170.

Figure 7:
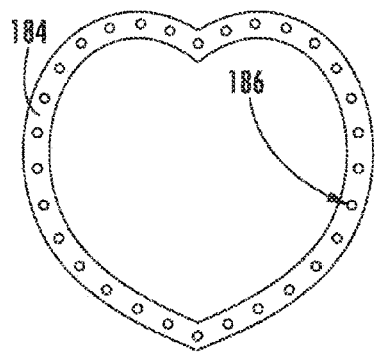
FIG. 7 shows a representative preferred embodiment of a connecting member 184 in a front view, which forms part of the preferred accessory securement system 172 illustrated in the FIG. 5 variation 100' of force-distributing cranial support 100.

Referring now to FIG. 7, the connecting member 184 comprises a plurality of pin receptacles 186 oriented along a face of the connecting member 184, the face being oriented distal to the force-distributing cranial support 100. The plurality of pin receptacles 186 may be configured as an internal indent.

Figure 8:
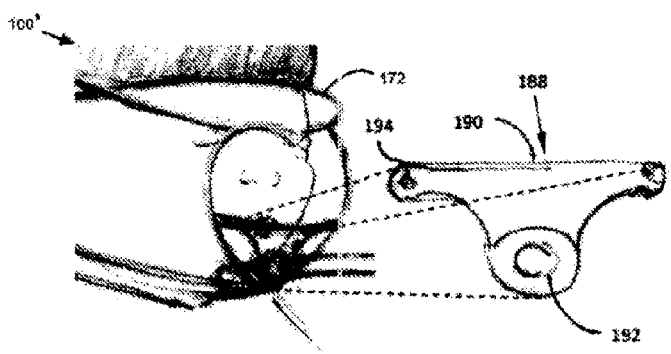
FIG. 8 shows a perspective view of a representative preferred embodiment of an accessory adapter 188, which is part of an alternative embodiment of the accessory securement system 172 illustrated in the FIG. 5 variation 100' of force-distributing cranial support 100.

Referring now to FIG. 8, the accessory securement system 172 further comprises an accessory adapter 188. The accessory adapter 188 is adapted with a transverse bar 190, which is formed integrally with an accessory receiver 192 as well as one or more bar connecting pins 194. The bar connecting pins 194 are located proximate to ends of the bar 190 and oriented perpendicular to a longitudinal axis of the bar 190. In a preferred embodiment, the accessory adapter 188 comprises two bar connecting pins 194 proximate opposite ends of the bar 190 and parallel to one another. The accessory acceptor 190 may be a clasp, port, holder, clamp, or other mechanism suitable to secure a patient care accessory used in the treatment of the subject. Examples of such patient care accessories include endotracheal tubes, continuous positive airway pressure (CPAP) masks, tracheostomy tubes, nasogastric tubes, sensor cables, or any other suitable catheter, cable, wire, mask, eyeshade, or other apparatus. The bar connecting pin 194 provides a secure but releasable connection to one of the plurality of pin receptacles 186 of the connecting member 184. In other embodiments, the connecting member 184 is hingedly connected to a covering element having the same shape as the connecting member 184, the covering element oriented to close down on the face of the connecting member 184 having the plurality of pin receptacles 186 in a latching manner to secure the bar 190 of the accessory adapter 188 in place.

Still referring to FIG. 8, the accessory acceptor 190, in an embodiment, comprises an acceptor body and an ovoid shaped aperture defined by the acceptor body, the acceptor body hingedly split in two pieces along a longitudinal axis of the aperture, permitting the acceptor body to accept one of the patient care accessories. The two pieces of the acceptor body are affixably connected via any acceptable method including latches, magnets, threaded screw and socket, clamps, elastic band, twist connector, or other suitable mechanism. In use, the accessory adaptor may be positioned on the connecting member 184 in a position to orient the patient care accessory appropriately for its intended use. By way of an example, the aperture of the accessory acceptor 190 may be positioned over a subject's mouth 218 in the event that the used patient care accessory is an endotracheal tube, or over a subject's nose 217 in the event that the used patient care accessory is a CPAP mask. In some embodiments, the acceptor body surrounding the aperture is coated in a colored marking material such as an ink that will mark the patient care accessory when the body of the accessory acceptor 190 is secured around the patient care accessory. In use, this may provide an indication if the patient care accessory position moves or changes relative to the acceptor body. By way of an example, should the endotracheal tube begin to become dislodged, the ink smears on the endotracheal tube now exposed from under the acceptor body, to provide a clearly visible indication to a clinician that the endotracheal tube may need to be repositioned in order to avert the risk of an unplanned extubation.

The use of the force-distributing cranial support 100 is now described. The force-distributing cranial support 100 may be deployed by a healthcare professional or a caregiver onto the subject's head 210. The deployment comprises selecting an appropriate size for the force-distributing cranial support 100 such that the patient oriented face 106 of the occipital cup portion 118 is essentially in contact with the back 213 of the subject's head 210 and the head strap portion 120 is able to fit around the forehead 214 of the subject's head 210. The healthcare professional or a caregiver places the occipital cup portion 118 on the back 213 (which encompasses the occipital region 212) of the subject's head 210 and affixes the first wing 124a to the second wing 124b.

In use, the head strap portion 120 is moderately tensioned so as to prevent or minimize shifting of the force-distributing cranial support 100. The healthcare professional or a caregiver may then rest the subject onto a surface such as a mattress, in an essentially supine position. This may be a prophylactic deployment if the healthcare professional or a caregiver believes that such a supine position may result in an unsuitable pressure concentration on the back 213 of the subject's head 210, leading perhaps to local ischemia and the subsequent risk of a pressure ulcer or to a pathophysiologic deformation of the subject's head 210 and the subsequent risk of plagiocephaly, brachycephaly, and dolichocephaly (referred to collectively as, "positional cranial molding" or, simply, "cranial molding").

The healthcare professional may periodically remove the force-distributing cranial support 100 from the subject's head 210 to visually assess the condition of the skin of the subject's head 210. This visual assessment may include an evaluation of signs of irritation, erythema, papules, edema, vesicular eruption, or diaphoresis. While the force-distributing cranial support 100 is removed from the subject's head 210, the healthcare professional may measure the circumference of the subject's head 210 to determine if a different sized force-distributing cranial support 100 is appropriate. Neonatal patients in particular and infants in general are likely to have a rapid rate of growth, necessitating the use of progressively larger implements. The force-distributing cranial support 100 may be constructed in a variety of sizes to accommodate subjects of different sizes.

The force-distributing cranial support 100, because of its various characteristics, disperses and distributes the pressure from the area of contact between the surface such as the mattress and the subject's head 210 to a broader area on the subject's head 210 thus lowering the imparted pressure. In other embodiments, the healthcare professional or a caregiver may interventionally deploy the force-distributing cranial support 100 in a similar manner upon observation of an onset of a pressure ulcer or other indication of local ischemia on the subject's head 210. In still other embodiments, the healthcare professional or a caregiver may interventionally deploy the force-distributing cranial support 100 in a similar manner upon observation of an onset of cranial molding.

A subject on whom the force-distributing cranial support 100 is deployed may be receiving critical medical care simultaneously. This care may include continuous positive airway pressure (CPAP), mechanical ventilation either through a tracheostomy or an orally placed endotracheal tube, enteral feeding, induced hypothermia, extracorporeal membrane oxygenation (ECMO), light therapy for hyperbilirubinemia, or other therapies that may utilize one or more accessories for delivery of the medical care. Similarly, these subjects may be instrumented for monitoring of physiologic variables possibly including oxygen saturation (Sp02), cerebral oxygenation, electroencephalography (EEG), skin temperature, tympanic temperature, or other physiologic variables that may utilize one or more lead wires or cables. The accessories and lead wires associated with the aforementioned therapies and monitoring modalities will preferably be secured about the subject's head. By way of example, in use, in a preferred embodiment, patients treated with mechanical ventilation would be intubated with an endotracheal tube that would be secured with the accessory adaptor in a manner restricting the migration of the endotracheal tube either out of the trachea or into the right mainstem bronchus. This may be useful in the case when the subject is a neonate for whom the endotracheal tube is uncuffed, in contradistinction to endotracheal tubes sized for use on adult subjects. The uncuffed endotracheal tube is more likely to migrate out of the patient resulting in an unplanned extubation and the subsequent cessation of mechanical ventilation. The semi-rigid yet resilient structure of the accessory securement system 172 or the elastic material of the cephalic or caudal arch members 137 allows for sufficient movement to reduce the risk of blunt trauma to soft tissue of the subject.

For instance, in a neonate, axial movement of a properly secured endotracheal tube may be limited to +/−15 mm or preferably +/−7 mm. By way of another example, the application of a multi-electrode EEG sensor with an associated lead wire set or cable may have its lead wire set or cable secured away from the skin of the subject on the accessory securement system 172 or on the cleat 178 of one of the anchor apparatus 170. Other monitoring modality lead wires or cables may be similarly secured. Similarly, tubing or catheters associated with enteral feeding, such as nasogastric tubes, may be secured to the accessory securement system 172 or on the cleat 178 of one of the anchor apparatus 170. Securing the aforementioned lead wires, cables, tubing, or catheters away from the subject may reduce the risk of pressure ulcers and may obviate the need for tape or adhesives to be applied to the skin of the subject.

EXAMPLES

In an unexpected finding, the gel layer 144 dimensioned between about 5 mm and about 10 mm in thickness was dramatically effective at distributing force in a simulated use both by decreasing peak pressure and by increasing the contact area. Indeed, it performs remarkably well in comparison to toroidal pressure distributing devices that are 50% to 400% thicker, dimensioned between about 15 mm and about 20 mm. However, despite being approximately two to three times thicker than the gel layer 144, toroidal pressure distributing devices provide no better pressure reduction. Moreover, the enveloping of the infant's head that the force-distributing cranial support 100 affords provides an inherent stability that may promote a safer or more comfortable environment.

Without being bound to a particular theory, the overall shape and fit of the force-distributing cranial support 100 in combination with the particular aqueous concentration of the gel layer 144 and relative thinness of the gel layer 144 are thought to contribute to the remarkable pressure reducing capabilities of the diminutive force-distributing cranial support 100.

Figure 9:
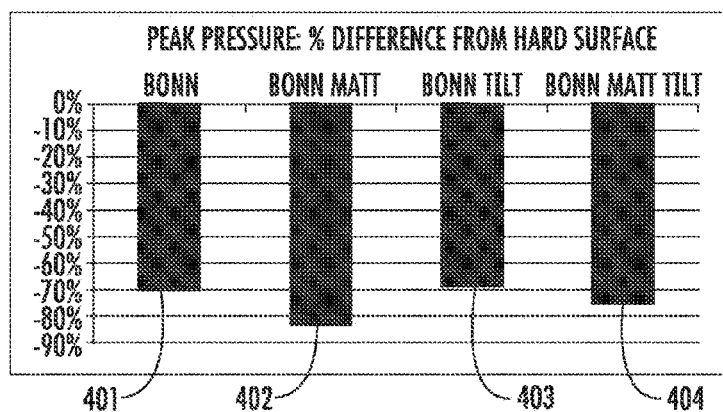
FIG. 9 shows a plot of the percent differences in peak pressures imparted to a subject positioned on a hard surface, the differences being between the peak pressures with and without the subject using a force-distributing cranial support comparable to support 100 of FIG. 1.
Figure 10:
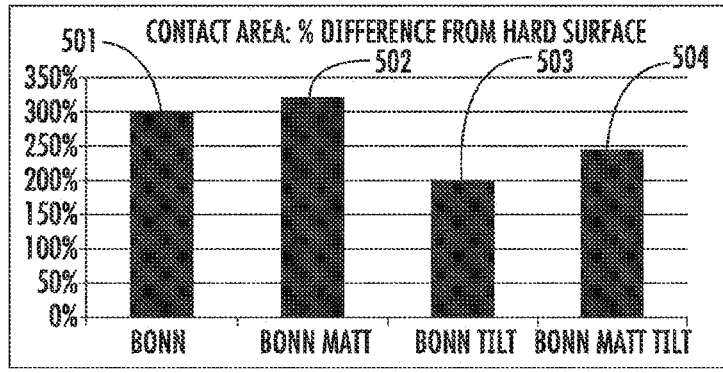
FIG. 10 shows a plot of the percent differences in contact areas between a subject and a hard surface, the differences being between the contact areas with and without the subject using a force-distributing cranial support comparable to support 100 of FIG. 1.

The plots shown in FIGS. 9 and 10 further illustrate the remarkable pressure reducing capabilities of force-distributing cranial support 100. As reflections of offloading capability on the back 213 of the head 210 of a neonatal infant 200, FIGS. 9 and 10 respectively illustrate percentage differences for the peak pressures and contact areas encountered at the points of contact for an infant baby doll (head circumference 12" and weight approximately 4 lbs) wearing a force-distributing cranial support 100 as generally described and illustrated in FIGS. 1-3.

To prepare the plots of FIGS. 9 and 10, pressure and contact area over time were evaluated using pressure sensors (Tekscan Fscan system) with and without the head 210 of the doll subject being fitted with force-distributing cranial support 100, and the difference with and without is represented in the respective FIGS. 9 and 10. FIG. 9 shows the percent differences in peak pressure encountered on the occipital region 212 of the head 210, when comparing use with and without the pressure-distributing cranial support 100, and FIG. 10 shows the corresponding percent differences in contact area with and without the pressure-distributing cranial support 100.

For added perspective, four support conditions are shown in each of FIGS. 9 and 10 (from left to right in each): (1) the left-most bars 401 and 501 representing the comparisons when supported on a hard horizontal surface (designated "Bonn"); (2) the second bars 402 and 502 representing the comparisons when supported on a horizontal infant mattress (designated "Bonn Matt"); (3) the third bars 403 and 503 representing the comparisons when supported on a hard surface that was tilted from the horizontal (designated "Bonn Tilt"); and (4) the fourth, right-most bars 404 and 504 representing the comparisons when supported on an infant mattress that was tilted from the horizontal (designated "Bonn Matt Tilt").

The study results illustrated in FIG. 9 revealed that all of the selected variables indicated significant off-loading of pressure and increased contact area on the back 213 of the baby doll head 210 for all conditions tested. The force-distributing cranial support 100 offloaded pressures 70% to 86% as illustrated by bars 401 and 402, respectively, in FIG. 9, and all peak pressure conditions were statistically significantly different from each other (see FIG. 9). When an infant mattress was introduced, as represented by both bars 402 and 404, the pressure offloading was further enhanced.

Moreover, despite the thin cross-sectional profile of the force-distributing cranial support 100, the contact area on the back 213 of the head increased between about a low of 220% and to a high of 340% for the conditions tested, as illustrated by bars 503 and 502, respectively, in FIG. 10, and all but one contact area variable was statistically significant from each other (see FIG. 10). When considering just the contact area, the force-distributing cranial support 100 on a mattress (bars 502 and 504) was not significantly different than the force-distributing cranial support 100 on a hard surface (bars 501 and 503, respectively), which may support a view that use of an infant mattress does not significantly influence the contact areas achieved through use of the force-distributing cranial support 100. While care was taken during data collection to reduce variability, the hard surface condition had higher levels of variability most likely due to variations on head and neck position of the baby doll. However, even with the variability, statistical significance was found.

A Tekscan pressure sensor was used to collect pressure profiles of the back of the head on an infant baby doll (head circumference 12" and weight approximately 4 lbs) for the force-distributing cranial support 100 on different surfaces (Hard surface, Infant Mattress—1" hard foam with vinyl cover) and for different positions (Laying down supine head vertical, Laying down supine head tilted between about 10° to 20°). The sensor was calibrated by wrapping it around a stainless steel cylinder and an air bladder was used to apply even pressure distribution to the sensor. The calibration was confirmed and adjusted by using a force transducer to apply a known force to the sensor.

During data collection, the sensor was taped to lessen sensor creasing prior to application of each condition. Twelve trials for each condition were collected for five minutes at one-second intervals. Variables of interest are total contact area, peak pressure value, and pressure mapping profile. Averages of the 12 trials for each surface and position were calculated.

The results for peak pressure showed a significant pressure reduction for all of the force-distributing cranial support 100 positions when compared to a hard surface. There was a significant difference in offloading peak pressures between the force-distributing cranial support 100 and a hard surface (69.8% and 78.7%) for both the vertical head and tilted head conditions. In the test condition with the mattress, the force-distributing cranial support 100 increases the reduction percentage to 83.7% for the head-vertical and 83.5% for the head-tilted condition relative to the hard surface. Range of peak pressure reduction for the head positions and surface conditions are from 69.8% to 83.7% reduction. A statistical t-test was used and statistical significance was found for all pressure variables.

In an unexpected finding, during a simulated infant movement test scenario, it was found that infant movement may dislodge the force-distributing cranial support 100. In the test scenario, the force-distributing cranial support 100 was secured to a head of a mannequin, shaped and sized similar to that of a neonatal infant, and this head was mechanically moved in a manner similar to that exhibited by a neonatal patient. A swaddling was placed in a position relative to base of the head of the mannequin as would be expected in a clinical environment. This dislodging of the force-distributing cranial support 100 occurred even as the force-distributing cranial support 100 was secured by means of the head strap portion 120 onto the mannequin, occurring either by the caudal edge 114 abutting swaddling typically used to wrap an infant during a back-arching movement or by the friction of the environmental oriented face 104 against bedding material during shifting of an infant, or both. It was surprisingly found that the separation of the caudal edge 114 of the force-distributing cranial support 100 relative to the proximate edge of the swaddling had a strong impact on the security and stability of the force-distributing cranial support 100. The measure of the caudal to cephalic curve of the occipital cup portion 118 then is a critical dimension. This critical dimension needs to extend sufficiently far to cover the occipital protuberance but not so far as to abut the expected position of swaddling. Further, the radius of the concavity of the occipital cup portion 118 is such that the occipital cup portion 118 is essentially in contact with the subject's head 210.

In another unexpected finding during this simulated infant movement test scenario, the low shear material of the patient oriented face 106 may have contributed to the force-distributing cranial support 100 becoming dislodged from the head of the mannequin in spite of the snug fit provided by the concave occipital cup portion 118 and the head strap portion 120. This finding was replicated in healthy human studies conducted under investigational review board oversight in which it was surprisingly found that the force-distributing cranial support 100 loosened as the infant moved over a sub-one hour period. The addition of the grip-providing substance 162 to the patient oriented face 106 in a revised design provided additional stability to the force-distributing cranial support 100 such that it remained secure on the head of the infant in the healthy human tests. This was a counterintuitive design change in that the focus had been on minimizing shear stress for the infant's skin until it was found that the addition of the grip-providing substance 162 to the patient oriented face 106 in an appropriate pattern resulted in no adverse events relative to skin integrity while providing sufficient stability of the force-distributing cranial support 100.

OTHER VARIATIONS AND COMMENTS

The invention may be embodied in other specific forms without departing from the spirit or essential characteristics thereof. As particular examples, many aspects of the invention will be appreciated through use of alternative embodiments that incorporate particular apparatus and methods of the prior applications that have been referenced and incorporated herein, or by use of select parts and subassemblies of such apparatus. The embodiments understood from the foregoing descriptions are therefore to be considered in all respects illustrative rather than limiting on the invention described herein. Indeed, numerous other features, objects, advantages, alternatives, variations, equivalents, substitutions, combinations, simplifications, elaborations, distributions, enhancements, improvements or eliminations (collectively, "variations") will be evident from these descriptions to those skilled in the art. Such variations will be especially evident when these descriptions are contemplated in light of a more exhaustive understanding of the numerous difficulties and challenges faced by the prior art.

All such variations should be considered within the scope of the invention, at least to the extent substantially embraced by the invention as defined in claims that may be associated with this application (including any added claims and any amendments made to those claims in the course of prosecuting this and related applications). In any case, the scope of the invention is thus indicated by such claims rather than by the foregoing description, and all changes that come within the meaning and range of equivalency of the claims are, therefore, intended to be embraced therein.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

We claim:

1. A force-distributing cranial support suitable for a head of an infant comprising:
    an occipital cup portion and an operatively attached head strap portion, said occipital cup portion and said head strap portion having a caudal edge adapted to be oriented towards a neck of an infant and a cephalic edge adapted to be oriented towards a crown of said head of said infant, wherein said force-distributing cranial support has a patient oriented face and an environmental oriented face, said patient oriented face comprising a material having hypoallergenic, biocompatible, non-irritating properties;
    a gel assembly oriented within said occipital cup portion, said gel assembly comprising a semi-solid material, said semi-solid material adapted to distribute a force of said head of said infant applied thereon, said semi-solid material containedly oriented within said gel assembly; and
    a padded layer, said gel assembly proximate said padded layer, wherein said padded layer and said gel assembly are elements of said occipital cup portion of said force-distributing cranial support;
    wherein said head strap portion is configured relative to said occipital cup such that said head strap portion is snugly conformable to a forehead of said infant while said occipital cup portion is operatively positioned adjacent to an occipital region of said head of said infant, said cephalic edge positioned below said crown of said head, whereby said crown of said head of said infant is uncovered.

2. The force-distributing cranial support of claim 1, wherein said environmental oriented face further comprises a medial environmental-face component, a first lateral environmental-face component, and a second lateral environmental-face component, said medial environmental-face component, said first lateral environmental-face component, and said second lateral environmental-face component being shaped with convex mutually facing edges such that when said mutually facing edges are affixed, said first lateral environmental-face component to said medial environmental-face component and said second environmental-face component also to said medial environmental-face component, said combined components of said environmental oriented face adopt a concave three-dimensional shape.

3. The force-distributing cranial support of claim 2, said gel assembly further comprising a medial gel element, a first lateral gel element, and a second lateral gel element, said medial gel element, and said first and second lateral gel elements securely maintained within an envelope sealed around a perimeter of said envelope, said gel assembly having flexing seams between said medial gel element and said first and second lateral gel elements.

4. The force-distributing cranial support of claim 3, wherein said envelope comprises a thermoplastic elastomer.

5. The force-distributing cranial support of claim 3, wherein said gel assembly is affixed to an inner surface of said environmental oriented face, said flexing seams of said gel assembly aligning with said mutually facing edges of said medial environmental-face component, said first lateral environmental-face component, and said second lateral environmental-face component, whereby said gel assembly assumes said concave three-dimensional shape of said environmental oriented face.

6. The force-distributing cranial support of claim 3, wherein said gel assembly further comprises an inferior gel element oriented towards said caudal edge and proximate to said medial gel element and said first and said second gel element, said inferior gel element maintained within said envelope.

7. The force-distributing cranial support of claim 1, further comprising a grip-providing substance fixedly applied on a portion of said patient oriented face, said grip-providing substance oriented to contact said head of said infant and adapted to facilitate and promote the securement of said force-distributing cranial support during normal movement of said infant.

8. The force-distributing cranial support of claim 7, wherein said grip-providing substance is a silicone.

9. The force-distributing cranial support of claim 7, wherein said grip-providing substance is applied to said patient oriented face on said occipital cup portion in a pattern around a perimeter of said occipital cup portion that leaves a center area of said patient oriented face uncovered by said grip-providing substance, whereby the grip-providing substance is configured such that when said infant is lying in a supine position, the peak pressure exerted on said head of said infant is exerted directly onto said patient oriented face rather than directly onto said grip-providing substance, and is further configured such that said grip-providing substance remains in contact with said head around said perimeter of said occipital cup portion.

10. The force-distributing cranial support of claim 1, wherein said occipital cup portion further comprises:
bilateral caudal tabs oriented on either side of said occipital cup portion along said caudal edge; and
bilateral ear accommodating arches oriented between said bilateral caudal tabs and said head strap portion,
wherein each of said bilateral ear accommodating arches are configured to be positioned proximate to a posterior aspect of an ear of said infant when said occipital cup portion is held adjacent to an occipital region of said head of said infant.

11. The force-distributing cranial support of claim 10, wherein said occipital cup portion is dimensioned between said bilateral ear-accommodating arches between about seven centimeters and about fifteen centimeters.

12. The force-distributing cranial support of claim 1, further comprising a caudal rim member, said caudal rim member oriented along said patient oriented face proximate said caudal edge of said occipital cup portion whereby said caudal rim member is configured to lie inferiorly to an occipital protuberance of said head of said infant when said occipital cup portion is held proximate said occipital region.

13. The force-distributing cranial support of claim 12, wherein a grip-providing substance is oriented on said caudal rim member.

14. The force-distributing cranial support of claim 1, wherein said semi-solid material is a hydrogel.

15. The force-distributing cranial support of claim 14, wherein said hydrogel contains a water concentration between about thirty-five percent and about fifty percent, whereby said concentration provides a resistance to flow and a resilience to compression from an externally applied force.

16. The force-distributing cranial support of claim 1, wherein said head strap portion further comprises a first wing and a second wing, each of said first and second wings extending from said occipital cup portion and configured to releasably attach said first wing to said second wing, across said forehead of said infant.

17. The force-distributing cranial support of claim 16, wherein said first wing further comprises a hook mechanism and said second wing further comprising a loop mechanism, said hook mechanism and said loop mechanism oriented to cooperatively operate whereby said first wing is releasably attachable to said second wing.

18. The force-distributing cranial support of claim 1, wherein said padded layer comprises a polyethylene foam.

19. The force-distributing cranial support of claim 1, wherein said padded layer further comprises a medial pad element, a first lateral paid element, and a second lateral pad element, said medial pad element, said first lateral pad element, and said second lateral pad element being shaped with convex mutually facing edges and being affixed to an inner surface of said environmental oriented face with said medial pad element aligned with said medial environmental-side component, said first lateral pad element aligned with said first lateral environmental-side component, and said second lateral pad element aligned with said second lateral environmental-side component.

20. The force-distributing cranial support of claim 1, wherein said occipital cup portion is dimensioned along an axis described from said cephalic edge to said caudal edge between about six centimeters and about nine centimeters.

21. The force-distributing cranial support of claim 1, further comprising a piping of a flexible piping material and a cord around which said flexible piping material is longitudinally wrapped, said flexible piping material stitched into said common perimeter of said patient oriented face and said environmental oriented face whereby said piping is affixed along at least a portion of said common perimeter.

22. The force-distributing cranial support of claim 1, further comprising an inner padded layer oriented between said gel assembly and said patient oriented face, said inner padded layer fixedly adhered to said patient oriented face and wherein said padded layer is proximate said occipital cup portion.

23. The force-distributing cranial support of claim 1, wherein said occipital cup portion has a thickness between about 5 millimeters and about 32 millimeters.

24. The force-distributing cranial support of claim 1, wherein said occipital cup portion has a thickness between about 8 millimeters and about 16 millimeters.

25. The force-distributing cranial support of claim 1, wherein said head strap portion extends from a side of said occipital cup portion, configured to wrap around said forehead of said infant and to releasably affix to a contralateral side of said occipital cup whereby said head strap is adapted to maintain said force-distributing cranial support in position around said head of said infant.

26. A force-distributing cranial support comprising:
a concave occipital cup portion and a head strap portion contiguously oriented with said occipital cup portion, said occipital cup portion and said head strap portion further comprising a patient oriented face and an environmental oriented face, said head strap portion adapted to fit around a forehead of an infant whereby said occipital cup is adapted to be brought into contact with a posterior aspect of a head of said infant;
a caudal edge oriented towards a neck of said infant and a cephalic edge adapted to be oriented towards a crown of said head of said infant; and
a gripping material, said gripping material affixed to said patient oriented face and adapted to be oriented to contact said head of said infant whereby said gripping material promotes resistance to movement of said head of said infant relative to said patient oriented face and, hence promotes resistance to movement of said head of said infant relative to said cranial deformation preventing device, wherein said gripping material has a thickness of between 50 microns and 250 microns;
wherein said occipital cup portion further comprises a force-distributing assembly of one or more force-distributing elements, said force-distributing assembly adapted to distribute a force at a contact point associated with a weight of said head of said infant when said head is placed in said occipital cup portion resting on a surface, whereby distributing the force over an area larger than said contact point reduces peak pressure;
wherein said patient oriented face further comprises a material having hypoallergenic, biocompatible, non-irritating properties.

27. The force-distributing cranial support of claim 26, wherein said gripping material covers a portion of said patient oriented face.

28. The force-distributing cranial support of claim 26, wherein said environmental-oriented face comprises a flexible textile.

29. A force-distributing cranial support suitable for a head of an infant comprising:
a head strap portion;
an occipital cup portion operatively attached to said head strap portion, said occipital cup portion further comprising bilateral caudal tabs and bilateral ear accommodating arches oriented between said bilateral caudal tabs and said head strap portion;
a caudal edge adapted to be oriented towards a neck of an infant and a cephalic edge adapted to be oriented towards a crown of a head of said infant;
a gel assembly formed to have a concave shape and comprising a gel element of a semi-solid material, said semi-solid material adapted to distribute a force of said head of said infant applied thereon, said gel element encapsulated within an envelope sealed around a perimeter of said envelope thereby maintaining said gel elements in a fixed orientation and location;
a padded layer forcibly adhered to said gel assembly, said padded layer being flexible, whereby said padded layer takes on said concave shape of said gel assembly; and
a patient oriented face and an environmental oriented face, said patient oriented face comprising a material having hypoallergenic, biocompatible, non-irritating properties, said patient oriented face having a grip-providing substance fixedly applied thereon, adapted to contact said head of said infant, and adapted to facilitate and promote the securement of the force-distributing cranial support during the normal movement of said infant, wherein said grip-providing substance has a thickness between 10 microns and 10 millimeters;
wherein said padded layer and said adhered gel assembly are elements of said occipital cup portion of the force-distributing cranial support;
wherein said head strap portion is oriented relative to said occipital cup portion such that said head strap portion is adapted to be snugly conformable to a forehead of said infant while said occipital cup portion is operatively positioned adjacent to an occipital region of said head of said infant, said cephalic edge configured to be positioned below said crown of said head, whereby said crown of said head of said infant is uncovered and each of said bilateral ear arches are positioned to be proximate a posterior aspect of an ear of said infant.

* * * * *